(12) United States Patent
Pereira et al.

(10) Patent No.: US 12,048,428 B2
(45) Date of Patent: Jul. 30, 2024

(54) DELIVERY TOOLS FOR MEDICAL IMPLANTS AND METHODS OF USING THE SAME

(71) Applicant: Boston Scientific Scimed, Inc., Maple Grove, MN (US)

(72) Inventors: Peter J. Pereira, Mendon, MA (US); Rebecca DeLegge, Mount Pleasant, SC (US); Lauren Eskew, Mount Pleasant, SC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 184 days.

(21) Appl. No.: 16/685,220

(22) Filed: Nov. 15, 2019

(65) Prior Publication Data

US 2020/0078009 A1    Mar. 12, 2020

Related U.S. Application Data

(63) Continuation of application No. 14/994,780, filed on Jan. 13, 2016, now Pat. No. 10,512,457.

(Continued)

(51) Int. Cl.
*A61B 17/04* (2006.01)
*A61B 17/06* (2006.01)
(Continued)

(52) U.S. Cl.
CPC ...... *A61B 17/0469* (2013.01); *A61B 17/0487* (2013.01); *A61B 17/06166* (2013.01);
(Continued)

(58) Field of Classification Search
CPC ............ A61B 17/0469; A61B 17/0487; A61B 17/06166; A61B 17/0619; A61B 2017/0488
See application file for complete search history.

(56) References Cited

U.S. PATENT DOCUMENTS 3,762,418 A   10/1973   Wasson
5,417,700 A    5/1995   Egan
(Continued)

FOREIGN PATENT DOCUMENTS

CN    101027013 A    8/2007
CN    101044996 A    10/2007
(Continued)

OTHER PUBLICATIONS

International Search Report and Written Opinion for PCT Application No. PCT/US2016/013393, mailed May 31, 2016, 16 pages.
(Continued)

*Primary Examiner* — Diane D Yabut
(74) *Attorney, Agent, or Firm* — Brake Hughes Bellermann LLP

(57) ABSTRACT

A medical device includes a filament having a first end portion and a second end portion. The first end portion of the filament is coupled to a needle. The medical device also includes an energy delivery device. The energy delivery device has a first arm and a second arm. The energy delivery device is configured to delivery energy to a portion of the filament when the portion of the filament is disposed between the first arm and the second arm.

19 Claims, 9 Drawing Sheets

Related U.S. Application Data

(60) Provisional application No. 62/104,281, filed on Jan. 16, 2015.

(51) Int. Cl.

| | | |
|---|---|---|
| A61B 17/00 | (2006.01) | |
| B29C 65/00 | (2006.01) | |
| B29C 65/02 | (2006.01) | |
| B29C 65/04 | (2006.01) | |
| B29L 31/00 | (2006.01) | |

(52) U.S. Cl.
CPC ............ *A61B 2017/00805* (2013.01); *A61B 2017/00858* (2013.01); *A61B 2017/0488* (2013.01); *A61B 2017/06033* (2013.01); *A61B 2017/06038* (2013.01); *A61B 2017/0608* (2013.01); *A61B 2017/0619* (2013.01); *B29C 65/02* (2013.01); *B29C 65/04* (2013.01); *B29C 66/69* (2013.01); *B29C 66/71* (2013.01); *B29L 2031/7546* (2013.01)

(56) References Cited

U.S. PATENT DOCUMENTS

| | | | |
|---|---|---|---|
| 5,509,923 A | | 4/1996 | Middleman et al. |
| 6,077,277 A | | 6/2000 | Mollenauer et al. |
| 6,368,343 B1 | | 4/2002 | Bonutti et al. |
| 7,166,570 B2 | | 1/2007 | Hunter et al. |
| 7,582,097 B2 | | 9/2009 | McRury et al. |
| 2002/0011508 A1 | | 1/2002 | Egan et al. |
| 2002/0173821 A1 | | 11/2002 | Fenton et al. |
| 2004/0210282 A1 | | 10/2004 | Flock et al. |
| 2005/0277984 A1 | | 12/2005 | Long |
| 2008/0255611 A1 | | 10/2008 | Hunter et al. |
| 2009/0036899 A1 | * | 2/2009 | Carlton ............ A61B 17/32056 606/29 |
| 2010/0104608 A1 | | 4/2010 | Abuzaina et al. |
| 2011/0264139 A1 | | 10/2011 | Hunter et al. |
| 2012/0191133 A1 | | 7/2012 | Ferree et al. |
| 2012/0245602 A1 | | 9/2012 | Glick et al. |
| 2013/0096611 A1 | | 4/2013 | Sullivan et al. |
| 2013/0158568 A1 | | 6/2013 | Kia et al. |
| 2014/0257027 A1 | | 9/2014 | Brent et al. |
| 2014/0276910 A1 | * | 9/2014 | Smith ................. A61B 17/221 606/113 |
| 2016/0174961 A1 | | 6/2016 | Callison et al. |
| 2016/0206308 A1 | | 7/2016 | Pereira et al. |
| 2016/0242763 A1 | | 8/2016 | Halpin et al. |
| 2016/0302788 A1 | | 10/2016 | Pereira et al. |
| 2017/0290650 A1 | | 10/2017 | Levinson |

FOREIGN PATENT DOCUMENTS

| | | |
|---|---|---|
| CN | 101045000 A | 10/2007 |
| CN | 101045004 A | 10/2007 |
| CN | 101305926 A | 11/2008 |
| CN | 101466315 A | 6/2009 |
| CN | 101686831 A | 3/2010 |
| CN | 101861129 A | 10/2010 |
| CN | 101902974 A | 12/2010 |
| CN | 107106163 A | 8/2017 |
| CN | 107427298 A | 12/2017 |
| EP | 3244805 A1 | 11/2017 |
| EP | 3285658 A1 | 2/2018 |
| WO | 2006084167 A1 | 8/2006 |
| WO | 2007089864 A2 | 8/2007 |
| WO | 2009086172 A2 | 7/2009 |
| WO | 2015050999 A1 | 4/2015 |
| WO | 2015089020 A1 | 6/2015 |
| WO | 2016171892 A1 | 10/2016 |

OTHER PUBLICATIONS

U.S. Appl. No. 14/994,780, filed Jan. 13, 2016, Allowed.

* cited by examiner

DELIVERY TOOLS FOR MEDICAL IMPLANTS AND METHODS OF USING THE SAME

CROSS-REFERENCE TO RELATED APPLICATIONS

This application is a continuation of, and claims priority to, U.S. patent application Ser. No. 14/994,780, filed on Jan. 13, 2016, entitled "DELIVERY TOOLS FOR MEDICAL IMPLANTS AND METHODS OF USING THE SAME", which claims priority to U.S. Provisional Patent Application No. 62/104,281, filed on Jan. 6, 2015, the disclosures of which are incorporated by reference herein in their entirety.

TECHNICAL FIELD

The present invention generally relates to surgical devices and procedures, particularly devices and methods for the attachment of implants or tissues within a body of a patient.

BACKGROUND

Anatomical tissues such as pelvic tissues may be weakened or damaged with age, injury, or disease. This decrease in structural integrity of anatomical tissues may have significant medical consequences, which in turn might influence the biological functions of the tissues. There are various surgical procedures for treating such dysfunction of the tissues. Implants can be placed into a patient to provide support for the weakened or damaged tissue. The support provided by the implant may replicate the natural position and structure of the tissue, and thereby help in decreasing or eliminating impairment of biological functions resulting from tissue weakening or damage.

Some medical procedures, such as a laparoscopic sacrocolpopexy, may be performed on a patient to address the issues of weakened or damaged pelvic tissue. Some such procedures require coupling or fixing an implant to a tissue wall, such as a vaginal wall. In some cases, sutures are used to couple or fix the implant to the vaginal wall. This process may be time intensive as it may be difficult to tie knots in the suture to couple or fix the implant to the tissue and often times many knots are required to be tied (such as at various locations along the implant).

In view of the above, there is a need for improved delivery tools and improved methods of delivering or placing implants within a body of a patient.

SUMMARY

A medical device includes a filament having a first end portion and a second end portion. The first end portion of the filament is coupled to a needle. The medical device also includes an energy delivery device. The energy delivery device has a first arm and a second arm. The energy delivery device is configured to delivery energy to a portion of the filament when the portion of the filament is disposed between the first arm and the second arm.

In some embodiments, the energy delivery device is configured to deliver heat energy to the portion of the filament. In some embodiments, the energy delivery device is configured to deliver radiofrequency energy to the portion of the filament.

In some embodiments, the filament is a suture. In some embodiments, the filament has a length extending from the first end portion to the second end portion, a width, and a thickness, the width of the filament being greater than the thickness of the filament. In some embodiments, the filament is formed of polyurethane or polyvinyl chloride.

In some embodiments, the needle includes a curved portion.

In some embodiments, the first arm of the energy delivery device is configured to move with respect to the second arm of the energy delivery device. In some embodiments, the energy delivery device includes an extension member that extends from the first arm of the energy delivery device to the second arm of the energy delivery device.

In some embodiments, the device includes an implant. In such embodiments, the implant may be attached within a body of a patient. In some embodiments, the implant is formed of a mesh material.

In some embodiments, the energy delivery device includes an actuator configured to cause the first arm to move with respect to the second arm when actuated. For example, the first arm may move, and the second arm may be fixed with respect to the body of the device or both arms may be movably coupled to a body of the device and may move when actuated. In some embodiments, the energy delivery device includes an actuator configured to activate energy to be delivered to the filament. In some embodiments, the energy delivery device includes a first actuator configured to cause the first arm to move with respect to the second arm when actuated and a second actuator configured to activate the energy to be delivered to the filament.

In some embodiments, a kit includes a filament having a first end portion and a second end portion, the first end portion of the filament being coupled to a needle; an energy delivery device, the energy delivery device having a first arm and a second arm, the energy delivery device being configured to deliver energy to a portion of the filament when the portion of the filament is disposed between the first arm and the second arm; and an implant configured to be placed within a body of a patient.

In some embodiments, the first arm of the energy delivery device is configured to move with respect to the second arm of the energy delivery device. In some embodiments, the energy delivery device includes an extension member that extends from the first arm of the energy delivery device to the second arm of the energy delivery device. In some embodiments, the energy delivery device is configured to deliver heat energy to the portion of the filament. In some embodiments, the energy delivery device is configured to deliver radiofrequency energy to the portion of the filament.

In some embodiments, a method of placing an implant within a body of a patient includes inserting the implant into the body of the patient such that the implant is disposed adjacent bodily tissue; passing a filament through the implant and through a portion of the bodily tissue; and applying energy to a first portion of the filament to fuse the first portion of the filament to a second portion of the filament.

In some embodiments, the method for applying energy includes inserting an energy delivery device into the body of the patient. In some embodiments, the method for applying energy includes inserting an energy delivery device into the body of the patient such that first portion of the filament is disposed between a first arm of the energy delivery device and a second arm of the energy delivery device. In some embodiments, the method for applying energy includes inserting an energy delivery device into the body of the patient such that first portion of the filament is disposed between a first arm of the energy delivery device and a second arm of the energy delivery device, and moving the first arm with respect to the second arm.

In some embodiments, the method includes cutting the filament such that a first segment of the filament remains coupled to the implant and the portion of the bodily tissue and a second segment, which is fixed to the needle, is free from the first segment of the filament; and passing the second segment of the filament though the implant and through a portion of the bodily tissue.

In some embodiments, the method includes passing a third portion of the filament through a fourth portion of the filament.

BRIEF DESCRIPTION OF THE DRAWINGS

The invention and the following detailed description of certain embodiments thereof may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

The terms proximal and distal described in relation to various medical devices, apparatuses, and components as discussed in the subsequent text of the present invention are referred with a point of reference. The point of reference, as used in this description, is a perspective of an operator. The operator may be a surgeon, a physician, a nurse, a doctor, a technician, and the like, who may perform the procedure or surgery through the patient's body orifice or incision as described in the present invention. The term proximal refers to an area that is closer to the operator. The term distal refers to an area that is farther from the operator. The patient, as referred to here, can be a human female, male or any other mammal.

Although the present invention focuses on devices, systems and methods for use primarily for treatment of urinary incontinence or other type of pelvic floor disorder, the disclosed devices, systems and methods may be used to treat any type of medical condition or be used in any other procedure to place an implant within a body of a patient. In some embodiments, the processes according to embodiments of the invention couple the implant to bodily tissue in a shorter amount of time than using a suture to tie knots to couple an implant to bodily tissue. In some embodiments, the pull-out force of the couplings is greater than 10 Newtons. In some embodiments, the procedures discussed below may be used via a laparoscopic device. As discussed below, in some embodiments, the devices may be used to couple the implant to bodily tissue at 10 or more or 12 or more locations.

Figure 1:
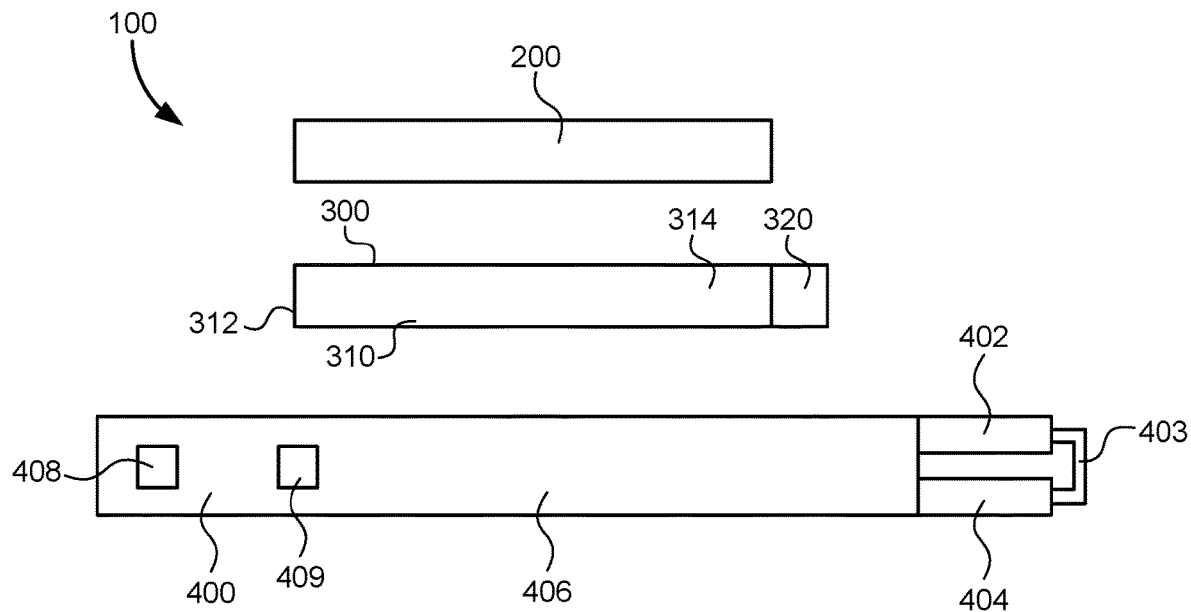
FIG. 1 is a schematic illustration of a medical device system according to an embodiment of the invention.

FIG. 1 is a schematic illustration of a medical system 100 according to an embodiment of the invention. The medical system 100 includes an implant 200, a filament system 300, and an energy delivery device 400. The items or devices of the medial system 100 may be packaged separately or may be packaged together as a kit. In some embodiments, only some of the items or devices are packaged together as a kit. For example, in some embodiments, only the filament system 300 and the energy delivery device 400 are packaged together as a kit. In other embodiments, other combinations of the items or devices are packaged together as a kit. In some embodiments, the kit may also include instructions for using the medical system 100.

The implant 200 may be placed within a body of a patient and coupled or fixed to bodily tissue within the body of the patient. For example, in some embodiments, the implant 200 may be inserted into the body of a patient and coupled to pelvic tissue or tissue within the pelvic region of the patient, such as a vaginal wall or tissue proximal to a vaginal wall of the patient. The implant 200 may be of any shape or size and may be formed of any type of biocompatible material. In some embodiments, the implant 200 is formed of a mesh material, such as a woven or knitted mesh.

The filament system 300 includes a filament 310 and a needle 320. In the illustrated embodiment, the filament 310 includes a first end portion 312 and a second end portion 314. The second end portion 314 is coupled to the needle 320. The needle 320 is configured to guide or lead the filament 310 through bodily tissue and through the implant 200.

The filament 310 is configured to extend through the implant 200 and though a portion of the bodily tissue of the patient. In some embodiments, as will be described in more detail below, a first portion the filament 310 is configured to extend through a second portion of the filament 310. In some embodiments, portions of the filament 310 may then be coupled to together to couple or fix the implant 200 to the bodily tissue.

In some embodiments, the filament 310 is formed of a material that is configured or formulated to accommodate the fusing of one portion of the filament 310 to another portion of the filament 310. For example, in some embodiments, the filament 310 may be formed of a material that is configured or formulated to have one portion of the filament 310 fuse to another portion of the filament 310 when energy, such as heat energy or radiofrequency (RF) energy or another type of energy, is applied to the portions of the filament 310. In some embodiments, the filament 310 is formed of or includes polyurethane. In other embodiments, the filament is formed of or includes polyvinylchloride (PVC). In yet other embodiments, the filament is formed of or includes one or more of the following materials: polypropylene, polyethylene, ABS polymers, acrylics, aclar, APET, Barex 210, Barex 218, butyrate, cellulose acetate (clear), cellulose acetate (color), cellulose acetate butyrate, cellulose nitrate, cellulose triacetate, ethylvinylacetate (EVA), ethylvinylalcohol (EVOH), melamine-formaldehyde resin, methylacrilate, nylon (polyamide), pelathane, polyethylene terphthate (PET), polyethylene terphthate glycol (PETG), polyamide, polymide, polymethyl (methacrylate), polystyrene, polyurethane, polyurethane-vinyl film, polyvinyl acetate, polyvinyl chloride (PVC) flexibleclear, and saran (polyvinylidene chloride). In some embodiment, the above materials are configured to facilitate the fusing of one portion of the filament 310 to another portion of the filament 310 when the portions of the filament are exposed to the energy (such as heat energy, RF energy, or another type of energy). The filament 310 may be formed of an absorbable (bioresorbable) material or a non-absorbable material (such as a bio-stable material). In some embodiments, the filament is formed of a bioabsorbable material such as polyglycolic acid (PGA), polyglactin (PGLA), poliglecaprone (PGCL), polydioxone (PDS), Poly(L-lactide-co-ε-caprolactone) (PLCL), Poly(glycerol sebacate) (PGS), strataprene (caprolactone/Llactide/glycolide/trmethylene carbonate polyaxial block), poly(L-lactic acid) (PLLA), poly(D,L-lactic acid or D,L-lactide) PDLLA, Poly(?-caprolacton-co-L-lactid) (PCL), poly(lactic-co-glycolic acid) (PLGA), Poly(DL-lactide-co-glycolide) (PDLGA), poly (L-co-D,L Lactic Acid) (PLDLA), Polycaprolactone (PLC), or Absory PLLA.

In some embodiments, the filament 310 may extend through the implant 200 and through a portion of the bodily tissue and the ends or portions of the filament 310 may be coupled or fused together to form a loop of filament thereby fixing or coupling the implant 200 to the bodily tissue. In some embodiments, the filament 310 may include a coating that is tacky or sticky (or is configured to stick to itself). In some embodiments, such adhesive coating may help hold the portions of the filament 310 together prior to the fusing of the portions. As will be described in more detail below, this holding of the portions of the filament 310 together may facilitate the process or step of fusing the portions of the filament 310 together.

The energy delivery device 400 is configured to deliver energy to portions of the filament 310. For example, once the filament 310 is passed through the implant 200 and the bodily tissue, the energy delivery device 400 may be used to delivery energy to ends or portions of the filament 310 to seal or fuse such portions of the filament 310 together. Accordingly, the filament 310 may form a complete loop of material to fix or couple the implant 200 to the bodily tissue. The energy delivery device 400 may be configured to delivery any type of energy to the portions of the filament 310. For example, in some embodiments, the energy delivery device 400 is configured to deliver heat energy to the portions of the filament 310. In other embodiments, the energy delivery device 400 is configured to deliver radiofrequency (RF) energy to the portions of the filament 310. In yet other embodiments, the energy delivery device 400 is configured to deliver another type of energy to the portions of the filament 310.

In some embodiments, the energy delivery device 400 includes a body or shaft portion 406 and arms or arm portions 402 and 404 that extend from the shaft portion 406. In some embodiments, the energy delivery device 400 is configured to deliver energy to portions of the filament 310 that are disposed between the arms or arm portions 402 and 404. In some embodiments, the arm portions are configured to move. For example, in some embodiments, the arms are configured to be in an open or spaced position to allow the portions of the filament 310 to be placed between the arms. One or both arms may then be moved (towards each other) to a closed position. In some embodiments, placing the arms in the closed position helps facilitate the holding of one portion of the filament adjacent a second portion of the filament prior to the fusing of the portions of the filament.

For example, in some embodiments, the energy delivery device 400 may include coils, strips, or other members coupled to or integrated with the arm portions 402 and 404. The coils, strips or other members may be configured to receive and/or deliver the energy (such as heat energy, RF energy, or another type of energy) to the filament 310.

In some embodiments, the energy delivery device 400 includes an extension member 403. The extension member 403 extends from the first arm 402 to the second arm 404 and is configured to help retain and align the portions of the filament within the arms 402 and 404 of the energy delivery device 400.

In some embodiments, the energy delivery device 400 includes a first actuation member 408 that is configured to activate the movement of the arms from the first or open position to the second or closed position. In some embodiments, the energy delivery device 400 also includes a second actuation member 409 that is configured to activate the energy that is to be delivered to the portions of the filament 310.

Figure 2:
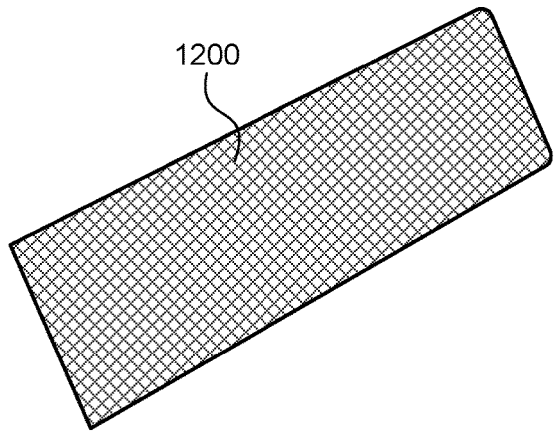
FIG. 2 is a perspective view of an implant according to an embodiment of the invention.

FIG. 2 is a perspective view of an implant 1200 according to an embodiment of the invention. The implant 1200 may be placed within a body of a patient and coupled or fixed to bodily tissue within the body of the patient. In some embodiments, the implant 1200 may be configured to help support or provide support to a portion of the body. For example, in some embodiments, the implant 1200 may be inserted into the body of a patient and coupled to pelvic tissue or tissue within the pelvic region of the patient, such as a vaginal wall or tissue proximal to a vaginal wall of the patient. Such an implant may be configured to provide support to a portion of the pelvic region of the patient, such as the bladder or the vagina of the patient.

The implant 1200 may be of any shape or size and may be formed of any type of biocompatible material. In the illustrated embodiment, the implant 1200 is rectangular and is formed as a mesh. In some embodiments, the mesh is a knitted mesh. In some embodiments, the mesh is Y-shaped.

Figure 3:
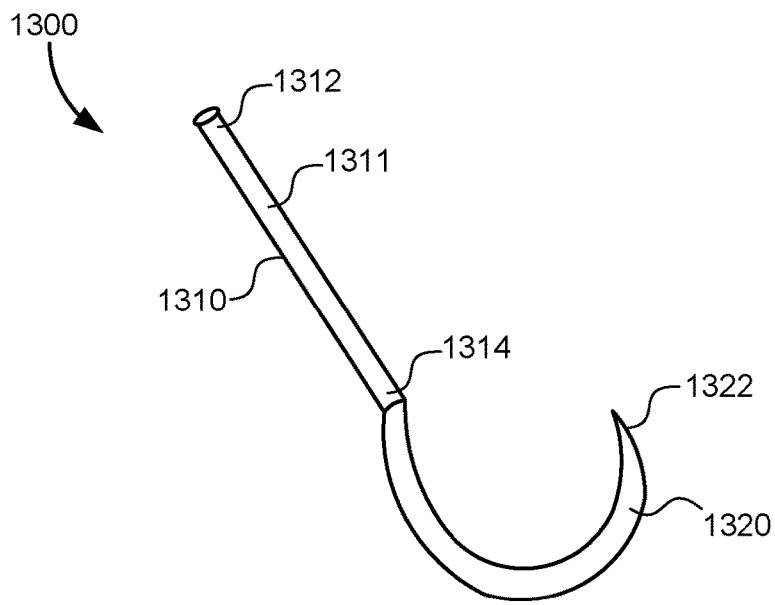
FIG. 3 is a perspective view of a filament coupled to a needle according to an embodiment of the invention.

FIG. 3 is a perspective view of a filament system 1300 according to an embodiment of the invention. The filament system 1300 includes a filament 1310 and a needle 1320. In the illustrated embodiment, the filament 1310 includes a first end portion 1312 and a second end portion 1314. The second end portion 1314 is coupled to the needle 1320. Any known method of coupling may be used to couple the second end portion 1314 to the needle 1320. For example, an adhesive, solder, or a swage joint may be used to couple the second end portion 1314 of the filament 1310 to the needle 1320.

The needle 1320 is configured to guide or lead the filament 1310 through the implant 1200 and the bodily tissue. In the illustrated embodiment, the needle 1320 includes a tapered or sharp portion 1322 that is configured to pierce bodily tissue to help guide the filament through the bodily tissue. In the illustrated embodiment, the needle 1320 includes a curved portion. In other embodiments, the needle is linear or includes a linear portion.

The filament 1310 is configured to extend through the implant 1200 and though a portion of the bodily tissue of the patient. Portions of the filament 1310 may then be coupled to together to fix the implant 1200 to the bodily tissue. The filament 1310 may be of any shape or size. In the illustrated embodiment, the filament 1310 is a tubular member (has a circular or oval cross section). In some embodiments, the filament 1310 is a suture. In some embodiments, the filament 1310 has a flat and relatively rectangular cross section (such as a film).

In some embodiments, the filament 1310 is formed of a material that is configured or formulated to accommodate the fusing of one portion of the filament 1310 to another portion of the filament 1310. For example, in some embodiments, the filament 1310 may be formed of a material that is configured or formulated to have one portion of the filament 1310 fuse to another portion of the filament 1310 when energy, such as heat energy or radiofrequency (RF) energy or another type of energy, is applied to the portions of the filament 1310. In some embodiments, the filament 1310 is formed of or includes polyurethane. In other embodiments, the filament 1310 is formed of or includes polyvinylchloride (PVC). In yet other embodiments, the filament 1310 is formed of or includes one or more of the following materials: ABS polymers, acrylics, aclar, APET, Barex 210, Barex 218, butyrate, cellulose acetate (clear), cellulose acetate (color), cellulose acetate butyrate, cellulose nitrate, cellulose triacetate, ethylvinylacetate (EVA), ethylvinylalcohol (EVOH), melamine-formaldehyde resin, methylacrilate, nylon (polyamide), pelathane, polyethylene terphthate (PET), polyethylene terphthate glycol (PETG), polyamide, polymide, polymethyl (methacrylate), polystyrene, polyurethane, polyurethane-vinyl film, polyvinyl acetate, polyvinyl chloride (PVC) flexibleclear, and saran (polyvinylidene chloride). In some embodiment, the above materials are configured to facilitate the fusing of one portion of the filament 1310 to another portion of the filament 1310 when the portions of the filament are exposed to the energy (such as heat energy, RF energy, or another type of energy). The filament 1310 may be formed of an absorbable (bioresorbable) material or a non-absorbable material (such as a bio-stable material). In some embodiments, the filament 1310 is formed of a bioabsorbable material such as polyglycolic acid (PGA), polyglactin (PGLA), poliglecaprone (PGCL), polydioxone (PDS), Poly (L-lactide-co-ε-caprolactone) (PLCL), Poly(glycerol sebacate) (PGS), strataprene (caprolactone/Llactide/glycolide/trmethylene carbonate polyaxial block), poly(L-lactic acid) (PLLA), poly(D,L-lactic acid or D,L-lactide) PDLLA, Poly (?-caprolacton-co-L-lactid) (PCL), poly(lactic-co-glycolic acid) (PLGA), Poly(DL-lactide-co-glycolide) (PDLGA), poly (L-co-D,L Lactic Acid) (PLDLA), Polycaprolactone (PLC), or Absory PLLA.

In some embodiments, the filament 1310 may extend through the implant 1200 and through a portion of the bodily tissue and back through the implant 1200 the ends or portions of the filament 1310 may be coupled or fused together to form a loop of filament thereby fixing or coupling the implant 1200 to the bodily tissue. In some embodiments, the filament 1310 may include a coating that is tacky or sticky (or is configured to stick to itself). For example, the filament 1310 may include a coating on the outer surface 1311 of the filament 1310. In some embodiments, only a portion of the outer surface 1311 includes the coating. In some embodiments, such adhesive coating may help hold the portions of the filament 1310 together prior to the fusing of the portions. As will be described in more detail below, this holding of the portions of the filament 1310 together may facilitate the process or step of fusing the portions of the filament 1310 together.

Figure 4:
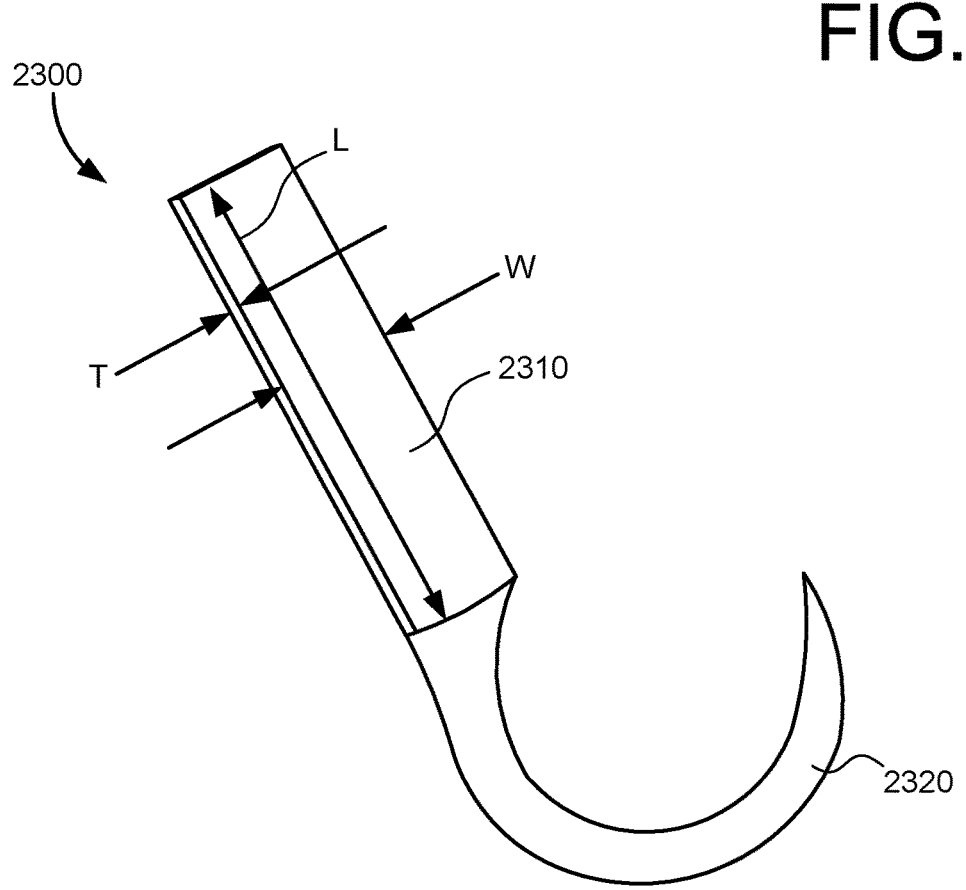
FIG. 4 is a perspective view of a filament coupled to a needle according to another embodiment of the invention.

FIG. 4 is a perspective view of a filament system 2300 in accordance with another embodiment of the invention. The filament system 2300 includes a filament 2310 that is coupled to a needle 2320. The filament 2310 is formed as a film or tape. In the illustrated embodiment the filament 2310 is a flat or planar film that has a length dimension L, a width dimension W, and a thickness dimension T. In the illustrated embodiment, the width dimension W is sufficient such that the filament 2310 or a portion of the filament 2310 may be passed through the filament along the width dimension W. In some embodiments, the length dimension L is greater than the width dimension W. Additionally, in some embodiments, the width dimension W is greater than the thickness dimension T. In some embodiments, the film or tape may be a solid member or may be a hollow member.

Figure 5:
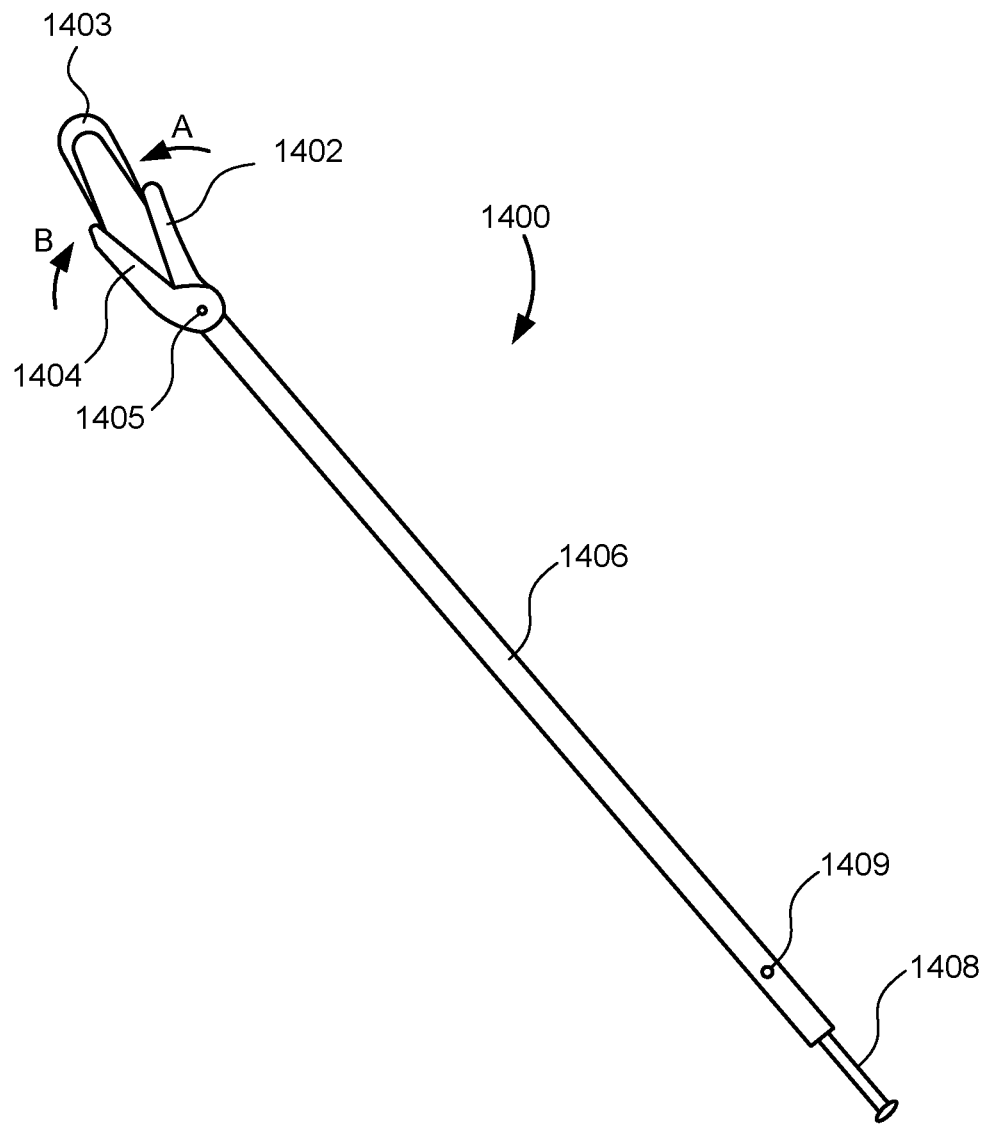
FIG. 5 is a perspective view of an energy delivery device according to an embodiment of the invention.

FIG. 5 is a perspective view of an energy delivery device 1400 in accordance with an embodiment of the invention. The energy delivery device 1400 is configured to be disposed or placed within a body of a patient and to deliver energy to portions of the filament. For example, once the filament is passed through the implant, the bodily tissue and back through the implant, the energy delivery device 1400 may be used to delivery energy to ends or portions of the filament to seal or fuse such portions of the filament together. Accordingly, the filament may form a complete loop of material to fix or couple the implant to the bodily tissue. The energy delivery device 1400 may be configured to deliver any type of energy to the portions of the filament. For example, in some embodiments, the energy delivery device 1400 is configured to deliver heat energy to the portions of the filament. In other embodiments, the energy delivery device 1400 is configured to deliver radiofrequency (RF) energy to the portions of the filament. In yet other embodiments, the energy delivery device 1400 is configured to delivery another type of energy to the portions of the filament.

In the illustrated embodiment, the energy delivery device 1400 includes a body or shaft portion 1406 and arms or arm portions 1402 and 1404 that extend from the shaft portion 1406. The energy delivery device 1400 is configured to deliver energy to portions of the filament that are disposed between the arms or arm portions 1402 and 1404. In some embodiments, only one of the arm portions 1402 and 1404 is configured to deliver energy to portions of the filament that are disposed between the arms or arm portions (and the other of the arm portions is configured to clamp or help retain the portions of the filament in place). In other embodiments, both of the arms or arm portions 1402 and 1404 are configured to deliver energy to portions of the filament that are disposed between the arms or arm portions.

In the illustrated embodiment, the arm portions are configured to move from a first or open position to a second or closed position. For example, arm portion 1402 is configured to move along or in the direction of arrow A. Arm portion 1404 is configured to move along or in the direction of arrow B. The arms are configured to be in the first (open or spaced) position to allow the portions of the filament to be placed between the arms 1402 and 1404. One or both arms may then be moved to the second or closed position. In some embodiments, placing the arms in the closed position helps facilitate the holding of one portion of the filament adjacent a second portion of the filament prior to the fusing of the portions of the filament.

In the illustrated embodiment, the energy delivery device 1400 includes an extension member 1403. The extension member 1403 extends from the first arm 1402 to the second arm 1404 and is configured to help retain and align the portions of the filament within or between the arms 1402 and 1404 of the energy delivery device 1400. In some embodiments, the extension member 1403 is configured to flex, retract or bend when the arms 1402 and 1404 are moved from their first or open position to their second or closed position.

In the illustrated embodiment, the arms 1402 and 1404 are pivotally coupled together at 1405. The energy delivery device 1400 includes a first actuation member 1408 that is configured to activate the movement of the arms 1402 and 1404 from the first or open position to the second or closed position. In the illustrated embodiment, the first actuation member 1408 is a plunger type actuator. The plunger or other leverage device (such as a trigger) may be pulled or moved to move the arms 1402 and 1404 from the first or open position to the second or closed position. In some embodiments, the actuation member 1408 is operatively coupled to the arms 1402 and 1404, for example via linkages and other members disposed within the body or shaft portion 1406 of the energy delivery device 1400. In some embodiments, the arms 1402 and 1404 are biased into one of the positions. For example, in some embodiments, the arms 1402 and 1404 are biased into the first or open positions.

In the illustrated embodiment, the energy delivery device 1400 also includes a second actuation member 1409 that is configured to activate the energy that is to be delivered to the portions of the filament. In the illustrated embodiment, the second actuation member 1409 is a button type actuation device or pedal from an external energy source. The second actuation member 1409 is operatively coupled to elements disposed on or within the arm portions 1402 and 1404 to deliver energy, such as heat energy or RF energy, to portions of the filament that are disposed between the arms 1402 and 1404.

Although the body or shaft portion 1406 of the energy delivery device 1400 is illustrated as being linear, in some embodiments, the body or shaft portion is curved or includes a curved portion. In some embodiments, the body or shaft portion has an articulation portion that is configured to bend or articulate.

Figure 6:
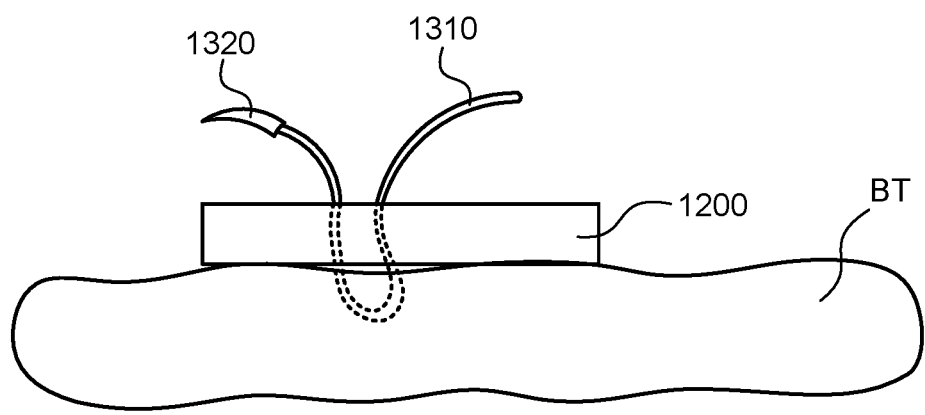
FIGS. 6-9 schematically illustrate a process of fixing or coupling an implant within a body of a patient according to an embodiment of the invention.

FIGS. 6-9 schematically illustrate a process of fixing or coupling an implant within a body of a patient according to an embodiment of the invention. As illustrated in FIG. 6, the implant 1200 may be placed within a body of a patient and disposed adjacent to bodily tissue BT. The filament 1310 may then be passed through the implant 1200, through the bodily tissue BT, and back through the implant 1200. In some embodiments, the filament 1310 does not extend entirely through the bodily tissue BT. For example, if the implant 1200 is being coupled or fixed to an outer surface of a vaginal wall of a patient, the filament need not pass entirely through the vaginal wall. In some cases, the filament will only be passed through a portion of the thickness of the vaginal wall.

Figure 7:
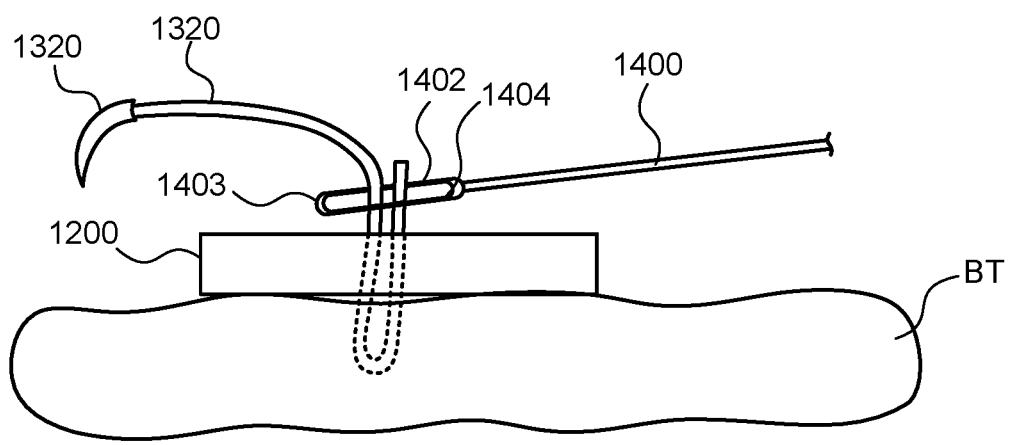

As illustrated in FIG. 7, portions of the filament 1310 may be disposed between the arms 1402 and 1404 of the energy delivery device 1400. The arms 1402 and 1404 may be moved to their closed positions to approximate the portions of the filament that are disposed between the arms. In some embodiments, when the arms 1402 and 1404 are disposed in their second or closed positions, the portions of the filament that are disposed between the arms are in contact with one another. The delivery device 1400 may then deliver energy to the portions of the filament 1310 that are disposed between the arms 1402 and 1404. The portions of the filament that receive the energy are configured to fuse together upon receiving the energy.

Figure 8:
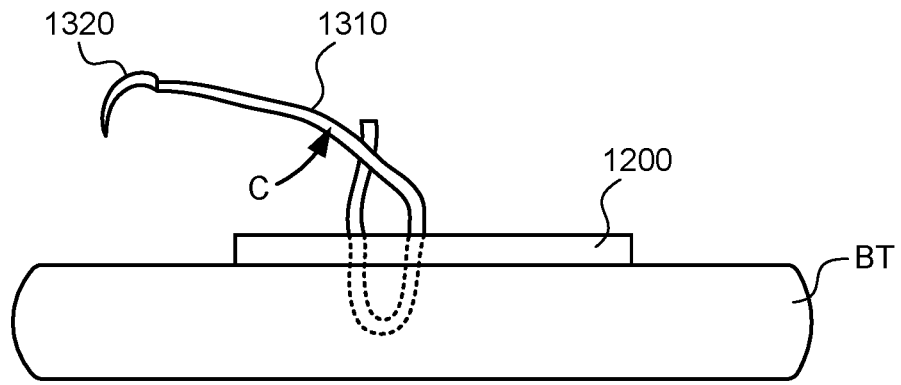

As illustrated in FIG. 8, the energy delivery device 1400 may be removed once the energy has been delivered and the portions of the filament have been fused or coupled together. The filament 1310 may then be cut, for example at location C. The remainder of the filament 1310 (the portion that remains attached to the needle 1320) may be used to repeat the above process to couple another portion of the implant 1200 to the bodily tissue BT. In some embodiments, the filament 1310 may be used to couple the implant 1200 to three, five, ten or more locations or portions of the bodily tissue BT.

Figure 9:
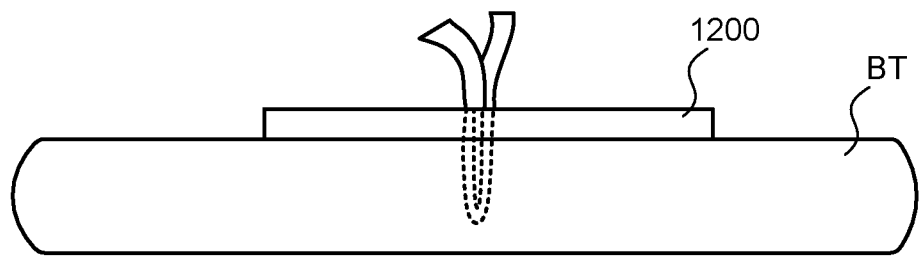

As illustrated in FIG. 9, the fused filament 1310 forms a complete loop through the implant 1200 and the bodily tissue BT. Accordingly, the implant 1200 is coupled to the bodily tissue BT.

Figure 10:
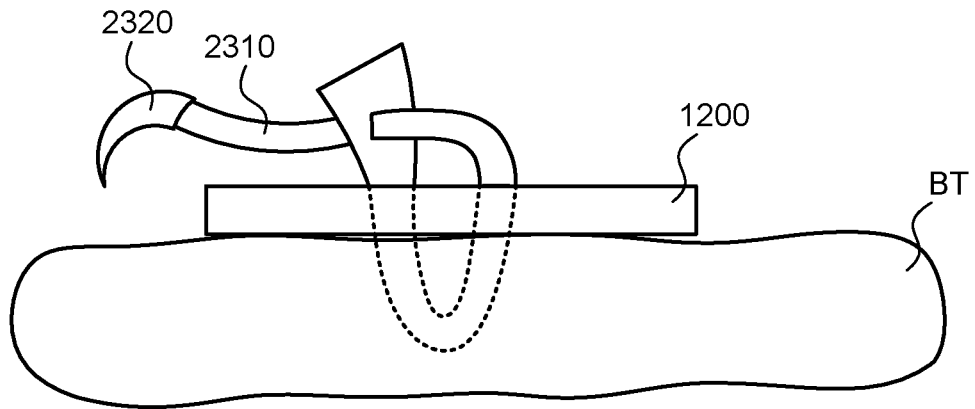
FIGS. 10-13 schematically illustrate a process of fixing or coupling an implant within a body of a patient according to another embodiment of the invention.

FIGS. 10-13 schematically illustrate a process of fixing or coupling an implant within a body of a patient according to another embodiment of the invention. As illustrated in FIG. 10, the implant 1200 may be placed within a body of a patient and disposed adjacent to bodily tissue BT. The filament 2310 (in the form of a wider film type filament) may then be passed through the implant 1200, through the bodily tissue BT, back through the implant 1200, and through a portion of the filament 2310 itself. In some embodiments, the passing of the filament 2310 back through a portion of itself may help retain the portions of the filament together prior to fusing of the portions and may facilitate the fusing process. In other embodiments, the passing of the filament 2310 back through a portion of itself may help facilitate the coupling or fusing of the portions together. In some embodiments, the filament 2310 does not penetrate the full thickness of the bodily tissue BT. For example, if the implant 1200 is being coupled or fixed to an outer surface of a vaginal wall of a patient, the filament need not pass entirely through the depth of the vaginal wall. In some cases, the filament will only be passed through a portion of the thickness of the vaginal wall.

Figure 11:
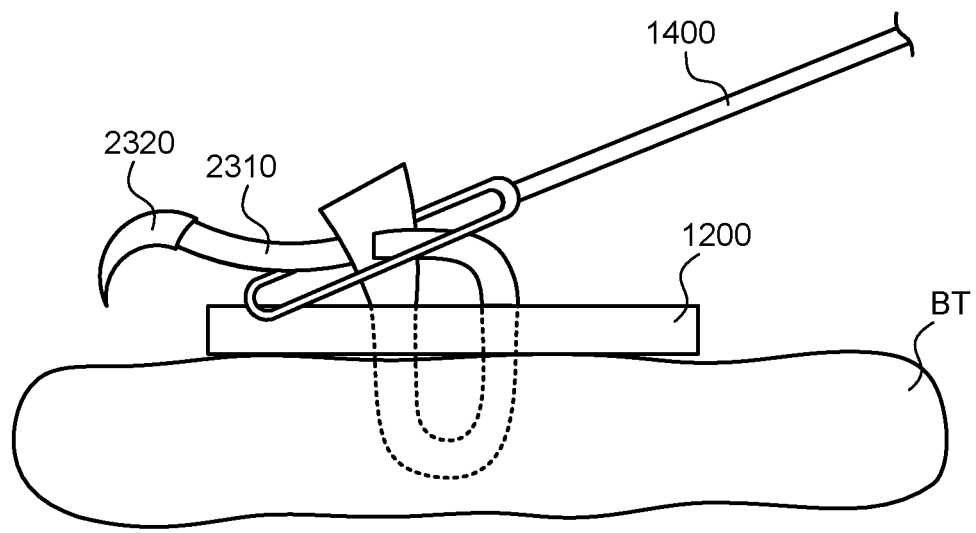

As illustrated in FIG. 11, portions of the filament 2310 may be disposed between the arms 1402 and 1404 of the energy delivery device 1400. The arms 1402 and 1404 may be moved to their closed positions to approximate the portions of the filament that are disposed between the arms. In some embodiments, when the arms 1402 and 1404 are disposed in their second or closed positions, the portions of the filament that are disposed between the arms are in contact with one another. The delivery device 1400 may then delivery energy to the portions of the filament 1310 that are disposed between the arms 1402 and 1404. The portions of the filament that receive the energy are configured to fuse together upon receiving the energy.

Figure 12:
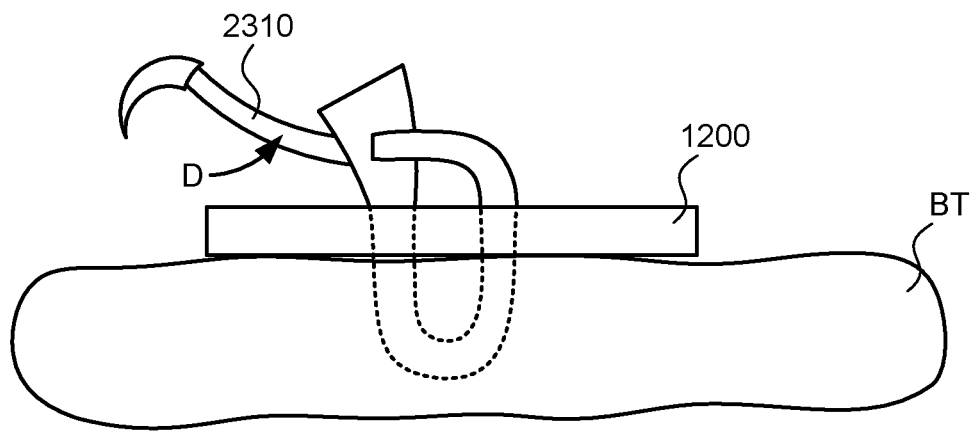

As illustrated in FIG. 12, the energy delivery device 1400 may be removed once the energy has been delivered and the portions of the filament have been fused or coupled together. The filament 2310 may then be cut, for example at location D. The remainder of the filament 2310 (the portion that remains attached to the needle 2320) may be used to repeat the above process to couple another portion of the implant 1200 to the bodily tissue BT. In some embodiments, the filament 2310 may be used to couple the implant 1200 to three, five, ten or more locations or portions of the bodily tissue BT.

Figure 13:
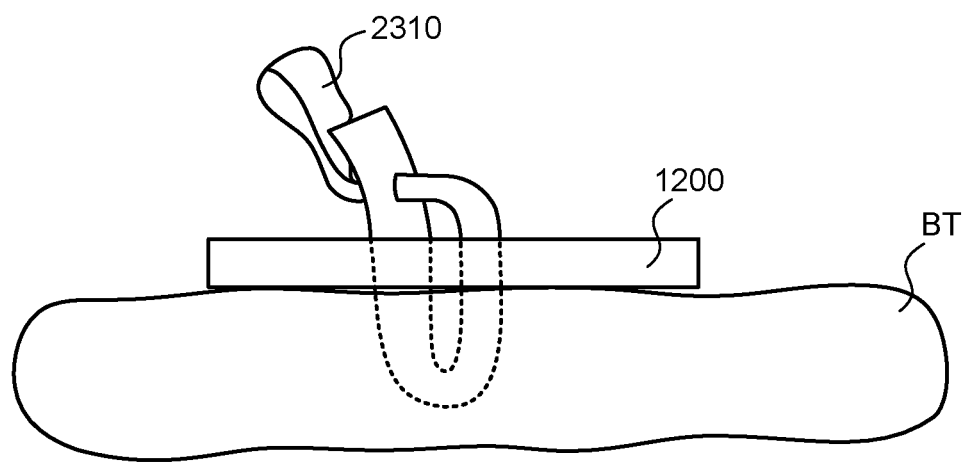

As illustrated in FIG. 13, the fused filament 2310 forms a complete loop through the implant 1200 and the bodily tissue BT. Accordingly, the implant 1200 is coupled to the bodily tissue BT.

Figure 14:
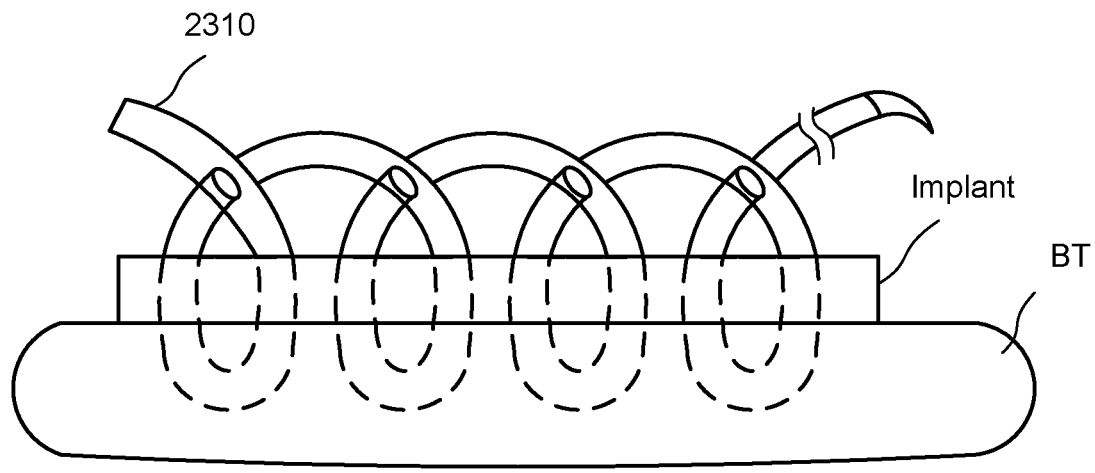
FIGS. 14 and 15 schematically illustrate a process of fixing or coupling an implant within a body of a patient according to another embodiment of the invention.
Figure 15:
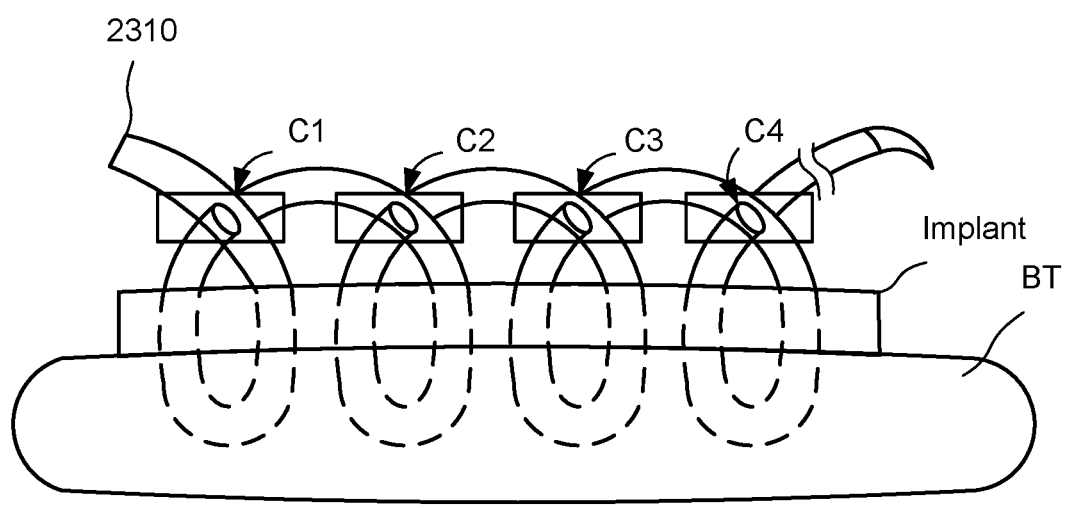

As illustrated in FIGS. 14 and 15, in some embodiments, the filament 2310 may be passed through the bodily tissue BT at several locations and passed through itself at several different locations (as illustrated in FIG. 14). For example, the filament 2310 may be passed through 2, 3, 4, or more different portions of the bodily tissue BT. Portions of the filament 2310 may then be fused or coupled together at substantially the same time. For example, the portions of the filament 2310 may be fused or coupled together serially without removing the energy delivery device 1400 from the body of the patient. For example, as illustrated in FIG. 15 the portions of the filament in boxes C1, C2, C3, and C4 may be coupled together using the energy delivery device 1400.

Figure 16:
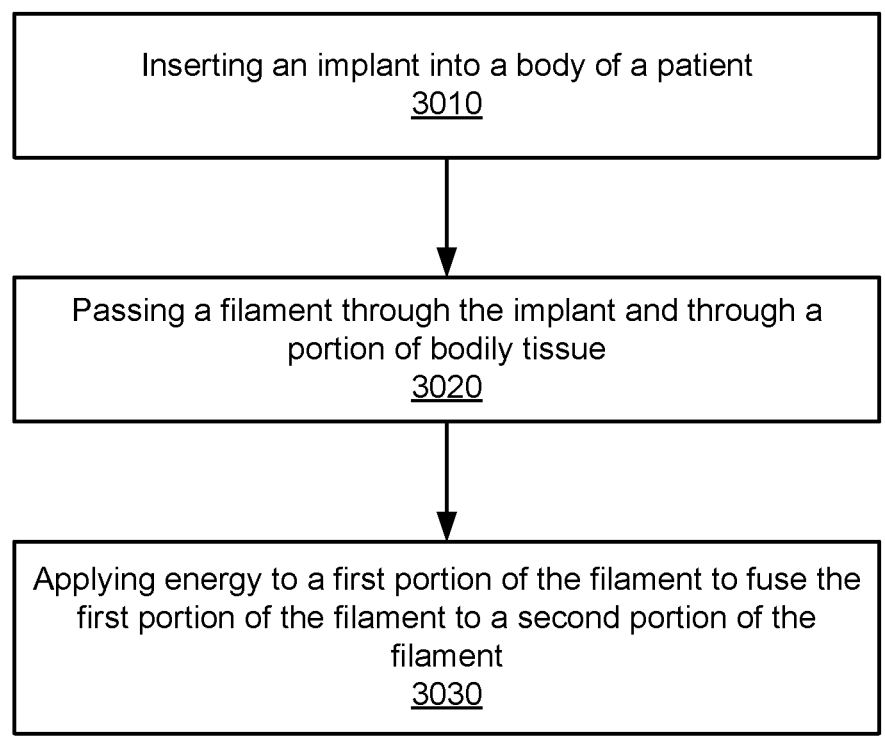
FIG. 16 is a flow chart illustrating a method according to an embodiment of the invention.

FIG. 16 is a flow chart illustrating a method 3000 according to an embodiment of the invention. The method includes at 3010, inserting an implant into a body of a patient. In some embodiments, the implant is disposed such that it is adjacent to bodily tissue such as a vaginal wall or bodily tissue proximal to a vaginal wall of a patient.

At 3020, a filament is passed through the implant and through the bodily tissue. At 3030, energy is applied to a first portion of the filament such that the first portion of the filament is fused to a second portion of the filament.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this invention. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the disclosure.

What is claimed is:

1. A medical device, comprising:
 a filament having a first end portion and a second end portion, the first end portion of the filament being coupled to a needle; and
 an energy delivery device, the energy delivery device having a handle, a first arm, and a second arm pivotally coupled to the first arm, the first arm having a distal end, the energy delivery device being configured to deliver energy to a portion of the filament, the energy delivery device includes an extension member that extends from the first arm of the energy delivery device to the second arm of the energy delivery device, the extension member extending to a location such that the distal end of the first arm is disposed between the handle and a portion of the extension member, the first arm, the second arm, and the extension member collectively defining an opening configured to receive the portion of the filament, the energy delivery device including an actuation member disposed on a shaft of the energy delivery device, the shaft of the energy delivery device defining a lumen, the first arm and the second arm being disposed outside of the lumen defined by the shaft, the energy delivery device having a plunger operatively coupled to the first arm and to the second arm and configured to pivot the first arm with respect to the second arm.

2. The medical device of claim 1, wherein the energy delivery device is configured to deliver heat energy to the portion of the filament.

3. The medical device of claim 1, wherein the energy delivery device is configured to deliver radiofrequency energy to the portion of the filament.

4. The medical device of claim 1, wherein the filament is a suture.

5. The medical device of claim 1, wherein the filament has a length extending from the first end portion to the second end portion, a width, and a thickness, the width of the filament being greater than the thickness of the filament.

6. The medical device of claim 1, wherein the filament is formed of polyurethane or polyvinyl chloride.

7. The medical device of claim 1, wherein the needle includes a curved portion.

8. The medical device of claim 1, wherein the first arm of the energy delivery device is configured to move with respect to the second arm of the energy delivery device.

9. The medical device of claim 1, wherein the first arm is configured to pivot with respect to the second arm about a pivot point.

10. A kit, comprising:
 a filament having a first end portion and a second end portion, the first end portion of the filament being coupled to a needle;
 an energy delivery device, the energy delivery device having a handle, a first arm, and a second arm pivotally coupled to the first arm, the energy delivery device being configured to deliver energy to a portion of the filament the energy delivery device includes an extension member that extends from the first arm of the energy delivery device to the second arm of the energy delivery device, the extension member extending to a location such that a distal end of the first arm is disposed between the handle and a portion of the extension member, the first arm, the second arm, and the extension member collectively defining an opening configured to receive the portion of the filament, the energy delivery device including an actuation member disposed on a shaft of the energy delivery device, the shaft of the energy delivery device defining a lumen, the first arm and the second arm being disposed outside of the lumen defined by the shaft, the energy delivery device having a plunger operatively coupled to the first arm and to the second arm and configured to pivot the first arm with respect to the second arm; and
 an implant configured to be placed within a body of a patient.

11. The kit of claim 10, wherein the first arm of the energy delivery device is configured to move with respect to the second arm of the energy delivery device.

12. The kit of claim 10, wherein the energy delivery device is configured to deliver heat energy to the portion of the filament.

13. The kit of claim 10, wherein the energy delivery device is configured to deliver radiofrequency energy to the portion of the filament.

14. The kit of claim 10, wherein the first arm is configured to pivot with respect to the second arm about a pivot point.

15. A method of placing an implant within a body of a patient, comprising:
inserting the implant into the body of the patient such that the implant is disposed adjacent bodily tissue;
passing a filament through the implant and through a portion of the bodily tissue;
inserting an energy delivery device into the body of the patient such that a first portion of the filament is disposed within an opening defined by a first arm of the energy delivery device, a second arm of the energy delivery device which is pivotally coupled to the first arm, and an extension member, the extension member extending to a location such that a distal end of the first arm is disposed between a handle portion and a portion of the extension member, the energy delivery device including an actuation member disposed on a shaft of the energy delivery device, the shaft of the energy delivery device defining a lumen, the first arm and the second arm being disposed outside of the lumen defined by the shaft, the energy delivery device having a plunger operatively coupled to the first arm and to the second arm and configured to pivot the first arm with respect to the second arm; and
actuating the actuation member to apply energy to the first portion of the filament to fuse the first portion of the filament to a second portion of the filament.

16. The method of claim 15, further comprising, actuating the plunger to pivot the first arm with respect to the second arm.

17. The method of claim 15, further comprising:
cutting the filament such that a first segment of the filament remains coupled to the implant and the portion of the bodily tissue and a second segment is free from the first segment of the filament; and
passing the second segment of the filament though the implant and through a portion of the bodily tissue.

18. The method of claim 15, further comprising:
passing a third portion of the filament through a fourth portion of the filament.

19. The method of claim 15, wherein the first arm is configured to pivot with respect to the second arm about a pivot point.

* * * * *